(12) United States Patent
Funderburk et al.

(10) Patent No.: US 11,103,716 B2
(45) Date of Patent: Aug. 31, 2021

(54) SYSTEMS AND METHODS FOR MAKING AND USING A LOW-PROFILE CONTROL MODULE FOR AN ELECTRICAL STIMULATION SYSTEM

(71) Applicant: Boston Scientific Neuromodulation Corporation, Valencia, CA (US)

(72) Inventors: Jeffery Van Funderburk, Stevenson Ranch, CA (US); Zdzislaw Bernard Malinowski, Castaic, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 300 days.

(21) Appl. No.: 16/186,058

(22) Filed: Nov. 9, 2018

(65) Prior Publication Data

US 2019/0143125 A1     May 16, 2019

Related U.S. Application Data

(60) Provisional application No. 62/585,405, filed on Nov. 13, 2017.

(51) Int. Cl.
*A61N 1/378* (2006.01)
*A61N 1/375* (2006.01)
(Continued)

(52) U.S. Cl.
CPC ......... *A61N 1/3787* (2013.01); *A61N 1/0529* (2013.01); *A61N 1/36017* (2013.01);
(Continued)

(58) Field of Classification Search
CPC ...... A61N 1/378; A61N 1/375; A61N 1/3752; A61N 1/3758
See application file for complete search history.

(56) References Cited

U.S. PATENT DOCUMENTS

| 979,652 A | 12/1910 | Church |
| 2,186,277 A | 1/1940 | Tetens |

(Continued)

FOREIGN PATENT DOCUMENTS

| EP | 0911061 | 4/1999 |
| JP | S55-112538 | 7/1980 |

(Continued)

OTHER PUBLICATIONS

International Search Report and Written Opinion for PCT Application No. PCT/US2018/060119 dated Feb. 12, 2019.

(Continued)

*Primary Examiner* — William J Levicky
(74) *Attorney, Agent, or Firm* — Branch Partners PLLC; Bruce E. Black

(57) ABSTRACT

A control module for an electrical stimulation system includes an electronic subassembly disposed within an electronics housing. A power assembly extends outwardly from the electronics housing and collectively with the electronics housing forms a sealed cavity. The power assembly includes a power source; a conduit assembly extending from the power source to the electronics housing; and one or more power conductors extending along the conduit assembly and electrically coupling the power source to the electronic subassembly. The control module further includes one or more connector assemblies. Each of the one or more connector assemblies includes a connector lumen configured to receive a lead; connector contacts arranged along the connector lumen and in electrical communication with the electronic subassembly; and connector conductors electrically coupled to the connector contacts.

20 Claims, 10 Drawing Sheets

(51) Int. Cl.
  *A61N 1/36*      (2006.01)
  *H02J 50/10*     (2016.01)
  *A61N 1/05*      (2006.01)
  *H01R 13/04*     (2006.01)
  *H01R 13/629*    (2006.01)

(52) U.S. Cl.
  CPC ............ *A61N 1/375* (2013.01); *A61N 1/378* (2013.01); *A61N 1/3752* (2013.01); *A61N 1/3758* (2013.01); *A61N 1/37514* (2017.08); *H01R 13/04* (2013.01); *H01R 13/629* (2013.01); *H02J 50/10* (2016.02); *A61N 1/0539* (2013.01); *A61N 1/0551* (2013.01); *A61N 1/3756* (2013.01)

(56) References Cited

U.S. PATENT DOCUMENTS

| | | | |
|---|---|---|---|
| 2,521,301 A | 9/1950 | Morrison | |
| 2,873,822 A | 2/1959 | Sloan | |
| 2,912,712 A | 11/1959 | Shamban et al. | |
| 3,758,827 A | 9/1973 | Schroder et al. | |
| 3,826,952 A | 7/1974 | Iwasaki et al. | |
| 3,829,737 A | 8/1974 | Johnsson | |
| 4,114,603 A | 9/1978 | Wilkinson | |
| 4,245,645 A | 1/1981 | Arseneault et al. | |
| 4,297,609 A | 10/1981 | Hirao et al. | |
| 4,315,180 A | 2/1982 | Kondo et al. | |
| 4,328,313 A | 5/1982 | Simonson et al. | |
| 4,328,813 A | 5/1982 | Ray | |
| 4,467,800 A | 8/1984 | Zytkoviez | |
| 4,741,571 A | 5/1988 | Godette | |
| 4,805,634 A | 2/1989 | Ullrich et al. | |
| 4,826,487 A | 5/1989 | Winter | |
| 4,850,359 A | 7/1989 | Putz | |
| 4,931,056 A | 6/1990 | Ghajar et al. | |
| 4,955,891 A | 9/1990 | Carol | |
| 4,998,938 A | 3/1991 | Ghajar et al. | |
| 5,116,345 A | 5/1992 | Jewell et al. | |
| 5,201,737 A | 4/1993 | Leibinger et al. | |
| 5,235,990 A | 8/1993 | Dempsey | |
| 5,300,080 A | 4/1994 | Clayman et al. | |
| 5,330,485 A | 7/1994 | Clayman et al. | |
| 5,464,446 A | 11/1995 | Dreessen et al. | |
| 5,484,445 A | 1/1996 | Knuth | |
| 5,496,356 A | 3/1996 | Hudz | |
| 5,503,164 A | 4/1996 | Friedman | |
| 5,549,620 A | 8/1996 | Bremer | |
| 5,556,421 A * | 9/1996 | Prutchi | A61N 1/37512 607/36 |
| 5,707,373 A | 1/1998 | Sevrain et al. | |
| 5,732,699 A | 3/1998 | Lundback | |
| 5,776,144 A | 7/1998 | Levsieffer et al. | |
| 5,800,504 A | 9/1998 | Bellifemine | |
| 5,843,150 A | 12/1998 | Dreessen et al. | |
| 5,865,842 A | 2/1999 | Knuth et al. | |
| 5,891,028 A | 4/1999 | Lundback | |
| 5,897,531 A | 4/1999 | Amirana | |
| 5,916,154 A | 6/1999 | Hobbs et al. | |
| 5,927,277 A | 7/1999 | Baudino et al. | |
| 5,954,687 A | 9/1999 | Baudino | |
| 5,984,930 A | 11/1999 | Maciunas et al. | |
| 5,993,463 A | 11/1999 | Truwit | |
| 6,006,124 A | 12/1999 | Fischell et al. | |
| 6,016,449 A | 1/2000 | Fischell et al. | |
| 6,044,304 A | 3/2000 | Baudino | |
| 6,050,098 A | 4/2000 | Meyer et al. | |
| 6,050,998 A | 4/2000 | Fletcher | |
| 6,073,048 A | 6/2000 | Kieval et al. | |
| 6,094,598 A | 7/2000 | Elsberry et al. | |
| 6,117,143 A | 9/2000 | Hynes et al. | |
| 6,126,663 A | 10/2000 | Hair | |
| 6,128,537 A | 10/2000 | Rise | |
| 6,128,538 A | 10/2000 | Fischell et al. | |
| 6,134,474 A | 10/2000 | Fischell et al. | |
| 6,134,477 A | 10/2000 | Knuteson | |
| 6,171,239 B1 | 1/2001 | Humphrey | |
| 6,175,710 B1 | 1/2001 | Kamaji et al. | |
| 6,181,969 B1 | 1/2001 | Gord | |
| 6,200,329 B1 | 3/2001 | Fung et al. | |
| 6,210,417 B1 | 4/2001 | Baudino et al. | |
| 6,224,450 B1 | 5/2001 | Norton | |
| 6,230,049 B1 | 5/2001 | Fischell et al. | |
| 6,269,266 B1 * | 7/2001 | Leysieffer | H04R 25/554 607/2 |
| 6,269,270 B1 | 7/2001 | Boveja | |
| 6,271,094 B1 | 8/2001 | Boyd et al. | |
| 6,284,729 B1 | 9/2001 | Bernfield et al. | |
| 6,295,944 B1 | 10/2001 | Lovett | |
| 6,308,101 B1 | 10/2001 | Faltys et al. | |
| 6,321,104 B1 | 11/2001 | Gielen et al. | |
| 6,324,433 B1 | 11/2001 | Errico | |
| 6,353,762 B1 | 3/2002 | Baudino et al. | |
| 6,354,299 B1 | 3/2002 | Fischell et al. | |
| 6,356,729 B1 | 3/2002 | Sasaki et al. | |
| 6,356,777 B1 | 3/2002 | Garfield et al. | |
| 6,356,792 B1 | 3/2002 | Errico | |
| 6,364,278 B1 | 4/2002 | Lin et al. | |
| 6,374,140 B1 | 4/2002 | Rise | |
| 6,391,985 B1 | 5/2002 | Goode et al. | |
| 6,413,263 B1 | 7/2002 | Lobdill et al. | |
| 6,427,086 B1 | 7/2002 | Fischell et al. | |
| 6,447,443 B1 | 9/2002 | Keogh et al. | |
| 6,459,936 B2 | 10/2002 | Fischell et al. | |
| 6,463,328 B1 | 10/2002 | John | |
| 6,464,687 B1 | 10/2002 | Ishikawa et al. | |
| 6,466,822 B1 | 10/2002 | Pless | |
| 6,480,743 B1 | 11/2002 | Kirkpatrick et al. | |
| 6,482,182 B1 | 11/2002 | Carroll et al. | |
| 6,516,227 B1 | 2/2003 | Meadows | |
| 6,560,486 B1 | 5/2003 | Osorio et al. | |
| 6,571,127 B1 | 5/2003 | Ben-Haim et al. | |
| 6,574,498 B1 | 6/2003 | Gilboa | |
| 6,597,954 B1 | 7/2003 | Pless et al. | |
| 6,609,020 B2 | 8/2003 | Gill | |
| 6,609,029 B1 | 8/2003 | Mann et al. | |
| 6,609,032 B1 | 8/2003 | Woods et al. | |
| 6,618,623 B1 | 9/2003 | Pless et al. | |
| 6,647,296 B2 | 11/2003 | Fischell et al. | |
| 6,690,974 B2 | 2/2004 | Archer et al. | |
| 6,741,892 B1 | 5/2004 | Meadows et al. | |
| 6,795,737 B2 | 9/2004 | Gielen et al. | |
| 6,845,257 B2 | 1/2005 | Fuimaono et al. | |
| 6,845,267 B2 | 1/2005 | Harrison et al. | |
| 6,895,280 B2 | 5/2005 | Meadows et al. | |
| 6,920,359 B2 | 7/2005 | Meadows et al. | |
| 6,944,501 B1 | 9/2005 | Pless | |
| 6,950,707 B2 | 9/2005 | Whitehurst | |
| 7,004,948 B1 | 2/2006 | Pianca et al. | |
| 7,033,326 B1 | 4/2006 | Pianca et al. | |
| 7,050,855 B2 | 5/2006 | Zeijlemaker et al. | |
| 7,090,661 B2 | 8/2006 | Morris et al. | |
| 7,146,222 B2 | 12/2006 | Boling | |
| 7,174,213 B2 | 2/2007 | Pless | |
| 7,174,219 B2 | 2/2007 | Wahlstrand et al. | |
| 7,177,701 B1 | 2/2007 | Pianca | |
| 7,204,840 B2 | 4/2007 | Skakoon et al. | |
| 7,235,084 B2 | 6/2007 | Skakoon et al. | |
| 7,244,150 B1 | 7/2007 | Brase et al. | |
| 7,343,205 B1 | 3/2008 | Pianca et al. | |
| 7,369,899 B2 | 5/2008 | Malinowski et al. | |
| 7,421,297 B2 | 9/2008 | Gifakis et al. | |
| 7,437,193 B2 | 10/2008 | Parramon et al. | |
| 7,450,997 B1 | 11/2008 | Pianca et al. | |
| 7,454,251 B2 | 11/2008 | Rezai et al. | |
| 7,479,146 B2 | 1/2009 | Malinowski et al. | |
| 7,529,586 B2 | 5/2009 | Wahlstrand et al. | |
| 7,548,775 B2 | 6/2009 | Kipke et al. | |
| 7,636,596 B2 | 12/2009 | Solar | |
| 7,672,734 B2 | 3/2010 | Anderson et al. | |
| 7,756,922 B2 | 7/2010 | Basu et al. | |
| 7,761,165 B1 | 7/2010 | He et al. | |
| 7,766,922 B1 | 8/2010 | Daglow et al. | |
| 7,783,359 B2 | 8/2010 | Meadows | |

(56) References Cited

U.S. PATENT DOCUMENTS

| | | |
|---|---|---|
| 7,787,945 B2 | 8/2010 | Greene |
| 7,792,590 B1 | 9/2010 | Pianca et al. |
| 7,809,446 B2 | 10/2010 | Meadows |
| 7,815,651 B2 | 10/2010 | Skakoon et al. |
| 7,833,231 B2 | 11/2010 | Skakoon et al. |
| 7,833,253 B2 | 11/2010 | Ralph et al. |
| 7,949,395 B2 | 5/2011 | Kuzma |
| 7,974,706 B2 | 7/2011 | Moffitt et al. |
| 8,150,537 B2 | 4/2012 | Tanaka et al. |
| 8,224,450 B2 | 7/2012 | Brase |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 8,473,061 B2 | 6/2013 | Moffitt et al. |
| 8,571,665 B2 | 10/2013 | Moffitt et al. |
| 8,688,235 B1 | 4/2014 | Pianca et al. |
| 8,792,993 B2 | 7/2014 | Pianca et al. |
| 9,278,208 B1 | 3/2016 | Gilson et al. |
| 9,440,070 B2 | 9/2016 | Goldwasser et al. |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0052610 A1 | 5/2002 | Skakoon et al. |
| 2002/0072770 A1 | 6/2002 | Pless |
| 2002/0077670 A1 | 6/2002 | Archer et al. |
| 2002/0099412 A1 | 7/2002 | Fischell et al. |
| 2002/0156372 A1 | 10/2002 | Skakoon et al. |
| 2002/0169485 A1 | 11/2002 | Pless et al. |
| 2003/0028199 A1 | 2/2003 | Ghahremani et al. |
| 2003/0083724 A1 | 5/2003 | Jog et al. |
| 2003/0088274 A1 | 5/2003 | Gliner et al. |
| 2003/0088303 A1 | 5/2003 | Goode |
| 2004/0034367 A1 | 2/2004 | Malinowski |
| 2004/0122446 A1 | 6/2004 | Solar |
| 2004/0153129 A1 | 8/2004 | Pless et al. |
| 2004/0172090 A1* | 9/2004 | Janzig .................. A61N 1/3754 607/45 |
| 2004/0176673 A1 | 9/2004 | Wahlstrand et al. |
| 2004/0176814 A1* | 9/2004 | Singhal .............. A61N 1/37514 607/45 |
| 2005/0010261 A1 | 1/2005 | Luders et al. |
| 2005/0015128 A1 | 1/2005 | Rezai et al. |
| 2005/0049646 A1 | 3/2005 | Luders et al. |
| 2005/0070458 A1 | 3/2005 | John |
| 2005/0075679 A1 | 4/2005 | Gliner et al. |
| 2005/0075680 A1 | 4/2005 | Lowry et al. |
| 2005/0092707 A1 | 5/2005 | Chantalat |
| 2005/0107753 A1 | 5/2005 | Rezai et al. |
| 2005/0182421 A1 | 8/2005 | Schulte et al. |
| 2005/0182422 A1 | 8/2005 | Schulte et al. |
| 2005/0182423 A1 | 8/2005 | Schulte et al. |
| 2005/0182424 A1 | 8/2005 | Schulte et al. |
| 2005/0182425 A1 | 8/2005 | Schulte et al. |
| 2005/0182464 A1 | 8/2005 | Schulte et al. |
| 2005/0222641 A1 | 10/2005 | Pless |
| 2005/0228249 A1 | 10/2005 | Boling |
| 2006/0129204 A1 | 6/2006 | Pless et al. |
| 2006/0190054 A1 | 8/2006 | Malinowski et al. |
| 2006/0190055 A1 | 8/2006 | Malinowski et al. |
| 2006/0212093 A1 | 9/2006 | Pless et al. |
| 2006/0224216 A1 | 10/2006 | Pless et al. |
| 2006/0229686 A1 | 10/2006 | Giftakis et al. |
| 2006/0247684 A1 | 11/2006 | Halperin et al. |
| 2007/0106143 A1 | 5/2007 | Flaherty |
| 2007/0150036 A1 | 6/2007 | Anderson |
| 2007/0173844 A1 | 7/2007 | Ralph et al. |
| 2007/0208352 A1 | 9/2007 | Henderson et al. |
| 2007/0225773 A1 | 9/2007 | Shen et al. |
| 2007/0233158 A1 | 10/2007 | Rodriguez |
| 2007/0265683 A1 | 11/2007 | Ehrlich |
| 2008/0071313 A1 | 3/2008 | Stevenson et al. |
| 2008/0086107 A1* | 4/2008 | Roschak ........... A61M 25/0068 604/506 |
| 2008/0100061 A1 | 5/2008 | Sage et al. |
| 2008/0172068 A1 | 7/2008 | Adams et al. |
| 2008/0243219 A1 | 10/2008 | Malinowski et al. |
| 2008/0275466 A1 | 11/2008 | Skakoon |
| 2009/0112327 A1 | 4/2009 | Lane et al. |
| 2009/0118804 A1 | 5/2009 | Moffitt et al. |
| 2009/0157157 A1 | 6/2009 | Schorn et al. |
| 2009/0182351 A1 | 7/2009 | Malinowski et al. |
| 2009/0187149 A1 | 7/2009 | Nelson |
| 2009/0187222 A1 | 7/2009 | Barker |
| 2009/0276021 A1 | 11/2009 | Meadows et al. |
| 2009/0281623 A1 | 11/2009 | Kast et al. |
| 2010/0023020 A1 | 1/2010 | Barker et al. |
| 2010/0023100 A1 | 1/2010 | Barker |
| 2010/0076535 A1 | 3/2010 | Pianca et al. |
| 2010/0145357 A1 | 6/2010 | Lane et al. |
| 2010/0268298 A1 | 10/2010 | Moffitt et al. |
| 2010/0280585 A1 | 11/2010 | Appenrodt et al. |
| 2010/0312193 A1 | 12/2010 | Stratton et al. |
| 2011/0004267 A1 | 1/2011 | Meadows |
| 2011/0005069 A1 | 1/2011 | Pianca |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0316615 A1 | 12/2012 | Digiore et al. |
| 2013/0006410 A1 | 1/2013 | Gentile et al. |
| 2013/0066430 A1 | 3/2013 | Funderburk |
| 2013/0066431 A1 | 3/2013 | Funderburk |
| 2013/0105071 A1 | 5/2013 | Digiore et al. |
| 2013/0197424 A1 | 8/2013 | Bedenbaugh |
| 2013/0197602 A1 | 8/2013 | Pianca et al. |
| 2014/0039587 A1 | 2/2014 | Romero |
| 2014/0257325 A1 | 9/2014 | Chavez et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0045864 A1 | 2/2015 | Howard |
| 2015/0051681 A1 | 2/2015 | Hershey |
| 2015/0066120 A1 | 3/2015 | Govea |
| 2015/0151113 A1 | 6/2015 | Govea et al. |
| 2016/0228692 A1 | 8/2016 | Steinke et al. |
| 2017/0021162 A1 | 1/2017 | Govea et al. |

FOREIGN PATENT DOCUMENTS

| | | |
|---|---|---|
| WO | 1998008554 | 3/1998 |
| WO | 1999055408 | 11/1999 |
| WO | 2000013743 | 3/2000 |
| WO | 2001/039830 | 6/2001 |
| WO | 20020045795 | 6/2002 |
| WO | 2003026738 | 4/2003 |
| WO | 20030028521 | 4/2003 |
| WO | 2004/052455 | 6/2004 |
| WO | 20040084749 | 10/2004 |
| WO | 2004105640 | 12/2004 |
| WO | 2005079903 | 9/2005 |
| WO | 2006031317 | 3/2006 |
| WO | 2008054691 | 5/2008 |
| WO | 2008054699 | 5/2008 |
| WO | 2008107815 | 9/2008 |
| WO | 2008107822 | 9/2008 |

(56) References Cited

FOREIGN PATENT DOCUMENTS

| WO | 2008134509 | 11/2008 |
|----|-----------|---------|
| WO | 2009055746 | 4/2009 |

OTHER PUBLICATIONS

Roberts DW. Hartov A. Kennedy FE, Miga MI, Paulsen KD: Intraoperative brain shift and deformation: A quantitative analysis of cortical displacement in 28 cases. Neurosurgery 43:749-760, 1998.
Dickhaus H., Ganser KA, Stuabert A., Bonsanto MM, Wirtz CR, Tronnier VM, Kunze S: Quantification of brain shift effects by MR-imaging. Engineering in Medicine and Biology Society vol. 2: 491-494, 1997.
Nimsky C., Gansland 0., Cerny S., Hastreiter P, Greiner G., Fahlbusch R.: Quantification of, visualization of, and compensation for brain shift using intraoperative magnetic resonance imaging. Neurosurgery 47, 1070-1080, 2000.
Winkler D., Tittgemeyer M., Schwartz J., Preul C., Strecker K., Meixensberger J.: The first evaluation of brain shift during functional neurosurgery by deformation field analysis. Journal of Neurology, Neurosurgery, and Psychiatry 76 (8): 1161-3, 2005.
Axelsson, Stefan et al., Longitudinal cephalometric standards for the neurocranium in Norwegians from 6 to 21 years of age, European Journal of Orthodontics, vol. 25 (2003) pp. 185-198.
Lieberman, Daniel E. et al., Basicranial influence on overall cranial shape, Journal of Human Evolution, vol. 38 (2000) pp. 291-315.

\* cited by examiner

SYSTEMS AND METHODS FOR MAKING AND USING A LOW-PROFILE CONTROL MODULE FOR AN ELECTRICAL STIMULATION SYSTEM

CROSS-REFERENCE TO RELATED APPLICATIONS

This application claims the benefit under 35 U.S.C. § 119(e) of U.S. Provisional Patent Application Ser. No. 62/585,405, filed Nov. 13, 2017, which is incorporated herein by reference.

FIELD

The present invention is directed to the area of implantable electrical stimulation systems and methods of making and using the systems. The present invention is also directed to a control module with an electronics housing and a power assembly that collectively form a sealed cavity, as well as methods of making and using the connector, control modules, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator) and one or more stimulator electrodes. The one or more stimulator electrodes can be disposed along one or more leads, or along the control module, or both. The stimulator electrodes are in contact with or near the nerves, muscles, or other tissue to be stimulated. The pulse generator in the control module generates electrical pulses that are delivered by the electrodes to body tissue.

BRIEF SUMMARY

In some aspects, a control module for an electrical stimulation system includes an electronics housing having an outer surface. An electronic subassembly is disposed within the electronics housing. A power assembly extends outwardly from the electronics housing and collectively with the electronics housing forms a sealed cavity. The power assembly includes a power source; a conduit assembly extending from the power source to the electronics housing; and one or more power conductors extending along the conduit assembly and electrically coupling the power source to the electronic subassembly. The control module further includes one or more connector assemblies. Each of the one or more connector assemblies includes a connector lumen configured to receive a lead; connector contacts arranged along the connector lumen and in electrical communication with the electronic subassembly; and connector conductors electrically coupled to the connector contacts.

In at least some embodiments, the conduit assembly includes a coupler and one or more tubular conduits extending from the coupler. The coupler is coupleable to the power source. The coupler and the one or more tubular conduits form a portion of the sealed cavity. The one or more power conductors extend through the one or more tubular conduits. In at least some embodiments, the one or more tubular conduits are flexible to permit bending relative to the electronics housing and power source upon application of a force and are configured to maintain a bent configuration. In at least some embodiments, the one or more tubular conduits are formed from a shape memory material. In at least some embodiments, the one or more tubular conduits include a bend forming an angle that is no smaller than 3° and no larger than 10°. In at least some embodiments, the angle of the bend corresponds to a contour of a portion of an outer surface of a skull to which the control module is attachable. In at least some embodiments, the electronics housing includes opposing parallel major surfaces extending along a first plane, and the bend causes the power assembly to extend along a second plane that is different from the first plane.

In at least some embodiments, feedthrough pins extend through the electronics housing, and the conductors of the one or more connector assemblies are electrically coupled to the feedthrough pins, and the feedthrough pins are electrically coupled to the electronic subassembly. In at least some embodiments, a charging coil is disposed external to the electronics housing and coupled to at least one of the feedthrough pins. In at least some embodiments, one or more antennas are disposed external to the electronics housing and coupled to at least one of the feedthrough pins.

In at least some embodiments, a covering is disposed over at least a portion of each of the electronics housing, the power assembly, and the one or more connector assemblies. In at least some embodiments, a fastener aperture is defined in the covering, the fastener aperture configured to receive a fastener for fastening the control module to an outer surface of a skull.

In at least some embodiments, when the control module is configured for fastening to an outer surface of a skull, the control module extends radially outwards from the outer surface of the skull by an amount no greater than 7 mm.

In other aspects, an electrical stimulation system includes any of the above-described control modules, and an electrical stimulation lead coupleable to the control module.

In yet other aspects, a method for making any of the above-described control modules includes disposing an electronic subassembly in an electronics housing. A power assembly having a power source is attached to at least one aperture defined in the electronics housing to create a sealed connection between the power assembly and the electronics housing. The power source is electrically coupled to the electronic subassembly. The electronics housing is sealed to, collectively with the power assembly, form a sealed cavity. A connector assembly is electrically coupled to the electronic subassembly. The connector assembly is configured to receive a lead.

In at least some embodiments, attaching a power assembly having a power source to at least one aperture defined in the electronics housing includes attaching the power source and the electronics housing to opposing ends of a conduit assembly. In at least some embodiments, the method further includes bending the conduit assembly relative to the electronics housing and power source. In at least some embodiments, the method further includes coupling a charging coil and one or more antennas to the electronic subassembly.

In still yet other aspects, a control module for an electrical stimulation system includes an electronics housing having an outer surface. An electronic subassembly is disposed within the electronics housing. A power assembly extends laterally outwardly from the electronics housing and collectively with the electronics housing forms a sealed cavity. The power assembly includes a power source; and one or more power conductors disposed entirely in the sealed cavity and electrically coupling the power source to the electronic subassembly. One or more connector assemblies extend laterally outwardly from the electronics housing. Each of the one or more connector assemblies includes a connector lumen configured to receive a lead; connector contacts arranged along the connector lumen and in electrical communication with the electronic subassembly; and connector conductors electrically coupled to the connector contacts.

In at least some embodiments, the one or more connector assemblies includes a first connector assembly and a second connector assembly each extending laterally outwardly from the electronics housing, where the first connector assembly and the second connector assembly flank the power assembly.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to a control module with an electronics housing and a power assembly that collectively form a sealed cavity, as well as methods of making and using the connector, control modules, and electrical stimulation systems.

Suitable implantable electrical stimulation systems include, but are not limited to, a least one lead with one or more electrodes disposed on a distal portion of the lead and one or more terminals disposed on one or more proximal portions of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734;7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, peripheral nerve, or cardiac-tissue) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for deep brain stimulation, but it will be understood that any of the leads can be used for applications other than deep brain stimulation, including spinal cord stimulation, peripheral nerve stimulation, dorsal root ganglion stimulation, sacral nerve stimulation, or stimulation of other nerves, muscles, and tissues.

Figure 1:
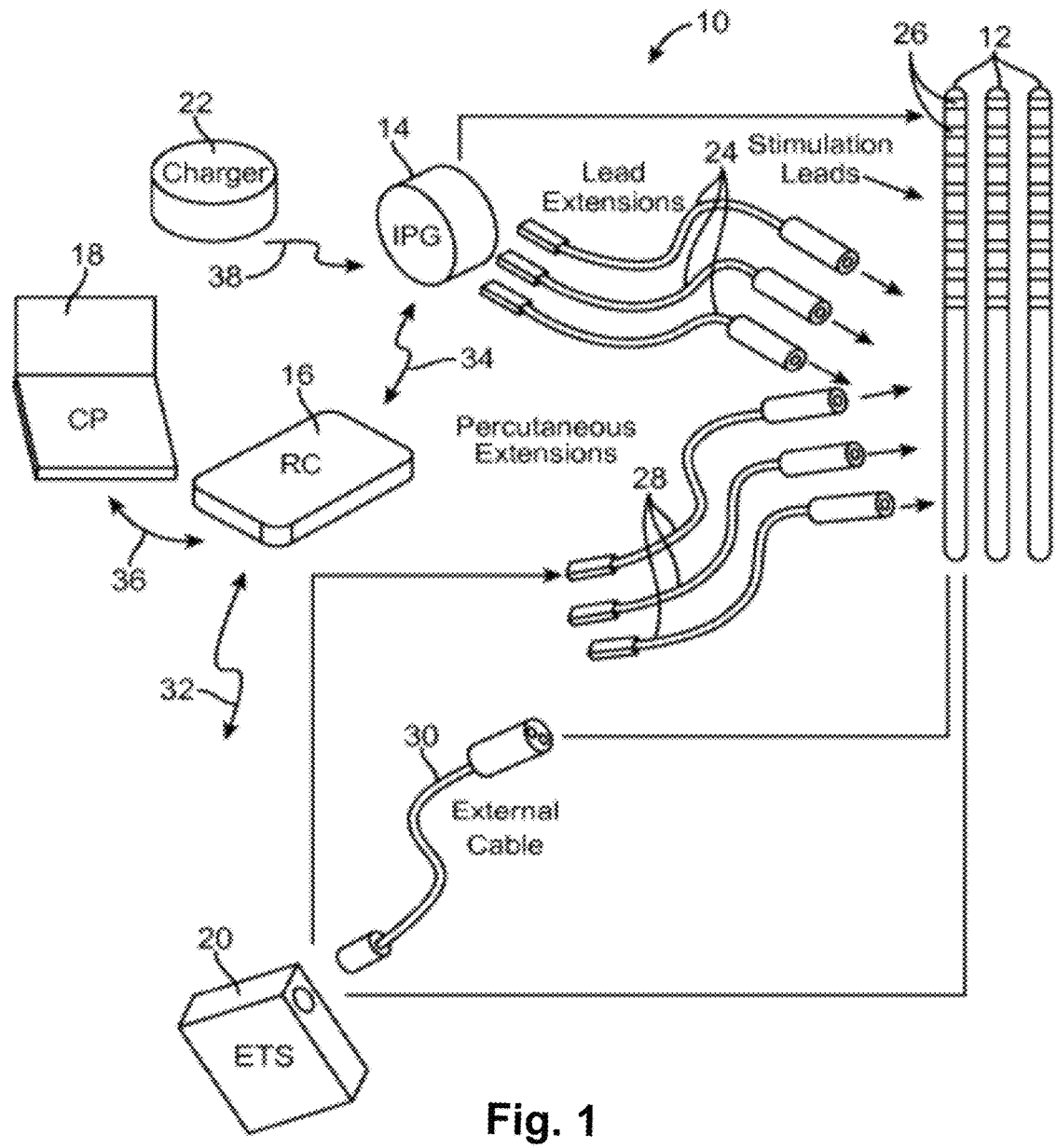
FIG. 1 is a schematic view of one embodiment of an electrical stimulation system, according to the invention.

Turning to FIG. 1, one embodiment of an electrical stimulation system 10 includes one or more stimulation leads 12 and an implantable pulse generator (IPG) 14.

The system 10 can also include one or more of an external remote control (RC) 16, a clinician's programmer (CP) 18, an external trial stimulator (ETS) 20, or an external charger 22.

The IPG 14 is physically connected, optionally, via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figure 2:
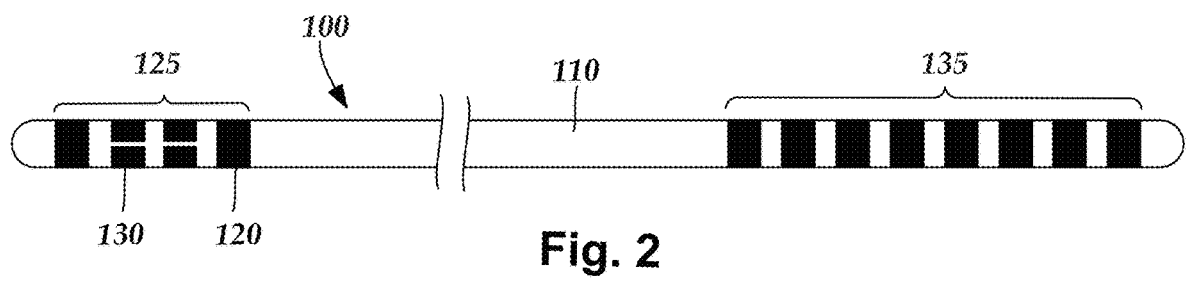
FIG. 2 is a schematic side view of one embodiment of an electrical stimulation lead, according to the invention.

Turning to FIG. 2, one or more leads are configured for coupling with a control module. The term "control module" is used herein to describe a pulse generator (e.g., the IPG 14 or the ETS 20 of FIG. 1). Stimulation signals generated by the control module are emitted by electrodes of the lead(s) to stimulate patient tissue. The electrodes of the lead(s) are electrically coupled to terminals of the lead(s) that, in turn, are electrically coupleable with the control module. In some embodiments, the lead(s) couple(s) directly with the control module. In other embodiments, one or more intermediary devices (e.g., a lead extension, an adaptor, a splitter, or the like) are disposed between the lead(s) and the control module.

Percutaneous leads are described herein for clarity of illustration. It will be understood that paddle leads and cuff leads can be used in lieu of, or in addition to, percutaneous leads. The leads described herein include 8 electrodes (+1 auxiliary electrode in some embodiments). It will be understood that the leads could include any suitable number of electrodes. The leads described herein exclusively include ring electrodes. It will be understood that the leads can include a distal-tip electrode, or one or more segmented electrodes in lieu of, or in addition to one or more ring electrodes. Additionally, the term "elongated member" used herein includes leads (e.g., percutaneous, paddle, cuff, or the like), as well as intermediary devices (e.g., lead extensions, adaptors, splitters, or the like).

FIG. 2 illustrates one embodiment of a lead 110 with electrodes 125 disposed at least partially about a circumference of the lead 110 along a distal end portion of the lead and terminals 135 disposed along a proximal end portion of the lead. The lead 110 can be implanted near or within the desired portion of the body to be stimulated such as, for example, the brain, spinal cord, or other body organs or tissues. In one example of operation for deep brain stimulation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of a stylet (not shown). The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, advance the lead 110, retract the lead 110, or rotate the lead 110.

In some embodiments, measurement devices coupled to the muscles or other tissues stimulated by the target neurons, or a unit responsive to the patient or clinician, can be coupled to the implantable pulse generator or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in, for example, tremor frequency or amplitude in response to stimulation of neurons. Alternatively, the patient or clinician can observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. In the embodiment of FIG. 2, two of the electrodes 125 are ring electrodes 120. Ring electrodes typically do not enable stimulus current to be directed from only a limited angular range around of the lead. Segmented electrodes 130, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead). To achieve current steering, segmented electrodes can be utilized in addition to, or as an alternative to, ring electrodes.

The lead 100 includes a lead body 110, terminals 135, and one or more ring electrodes 120 and one or more sets of segmented electrodes 130 (or any other combination of electrodes). The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes 125 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Patents Nos. 8,473,061; 8,571,665; and 8,792,993; U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/0197375; 2012/0203316; 2012/0203320; 2012/0203321; 2013/0197424; 2013/0197602; 2014/0039587; 2014/0353001; 2014/0358208; 2014/0358209; 2014/0358210; 2015/0045864; 2015/0066120; 2015/0018915; 2015/0051681; U.S. patent applications Ser. Nos. 14/557,211 and 14/286,797; and U.S. Provisional Patent Application Ser. No. 62/113,291, all of which are incorporated herein by reference. Segmented electrodes can also be used for other stimulation techniques including, but not limited to, spinal cord stimulation, peripheral nerve stimulation, dorsal root ganglion stimulation, or stimulation of other nerves, muscles, and tissues.

Figure 3:
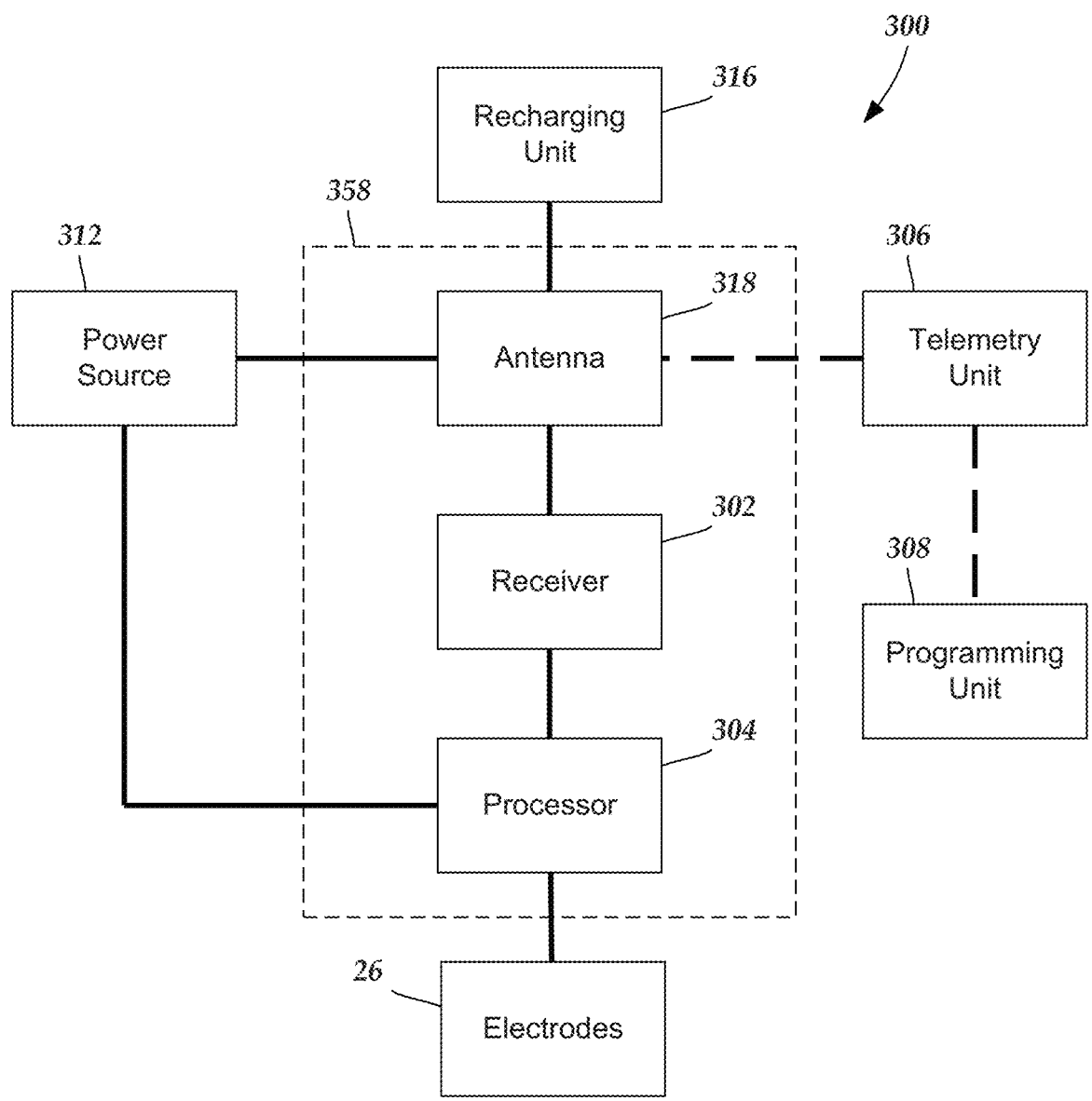
FIG. 3 is a schematic overview of one embodiment of components of a stimulation system, including an electronic subassembly disposed within a control module, according to the invention.

FIG. 3 is a schematic overview of one embodiment of components of an electrical stimulation system 300 including an electronic subassembly 358 disposed within a control module. The electronic subassembly 358 may include one or more components of the IPG. It will be understood that the electrical stimulation system can include more, fewer, or different components and can have a variety of different configurations including those configurations disclosed in the stimulator references cited herein.

Some of the components (for example, a power source 312, one or more antennas 318, a receiver 302, and a processor 304) of the electrical stimulation system can be positioned on one or more circuit boards or similar carriers within a sealed electronics housing of an implantable pulse generator (see e.g., 14 in FIG. 1), if desired. Any power source 312 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 318 or a secondary antenna. In at least some embodiments, the antenna 318 (or the secondary antenna) is implemented using the auxiliary electrically-conductive conductor. The external power source can be in a device that is mounted on the skin of the user or in a unit that is provided near the user on a permanent or periodic basis.

If the power source 312 is a rechargeable battery, the battery may be recharged using the optional antenna 318, if desired. Power can be provided to the battery for recharging by inductively coupling the battery through the antenna to a recharging unit 316 external to the user. Examples of such arrangements can be found in the references identified above. The electronic subassembly 358 and, optionally, the power source 312 can be disposed within a control module (e.g., the IPG 14 or the ETS 20 of FIG. 1).

In one embodiment, electrical stimulation signals are emitted by the electrodes (e.g., 26 in FIG. 1) to stimulate nerve fibers, muscle fibers, or other body tissues near the electrical stimulation system. The processor 304 is generally included to control the timing and electrical characteristics of the electrical stimulation system. For example, the processor 304 can, if desired, control one or more of the timing, frequency, strength, duration, and waveform of the pulses. In addition, the processor 304 can select which electrodes can be used to provide stimulation, if desired. In some embodiments, the processor 304 selects which electrode(s) are cathodes and which electrode(s) are anodes. In some embodiments, the processor 304 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 308 that, for example, allows modification of pulse characteristics. In the illustrated embodiment, the processor 304 is coupled to a receiver 302 which, in turn, is coupled to the optional antenna 318. This allows the processor 304 to receive instructions from an external source to, for example, direct the pulse characteristics and the selection of electrodes, if desired.

In one embodiment, the antenna 318 is capable of receiving signals (e.g., RF signals) from an external telemetry unit 306 which is programmed by the programming unit 308. The programming unit 308 can be external to, or part of, the telemetry unit 306. The telemetry unit 306 can be a device that is worn on the skin of the user or can be carried by the user and can have a form similar to a pager, cellular phone, or remote control, if desired. As another alternative, the telemetry unit 306 may not be worn or carried by the user but may only be available at a home station or at a clinician's office. The programming unit 308 can be any unit that can provide information to the telemetry unit 306 for transmission to the electrical stimulation system 300. The programming unit 308 can be part of the telemetry unit 306 or can provide signals or information to the telemetry unit 306 via a wireless or wired connection. One example of a suitable programming unit is a computer operated by the user or clinician to send signals to the telemetry unit 306.

The signals sent to the processor 304 via the antenna 318 and the receiver 302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 300 to cease operation, to start operation, to start charging the battery, or to stop charging the battery. In other embodiments, the stimulation system does not include the antenna 318 or receiver 302 and the processor 304 operates as programmed.

Optionally, the electrical stimulation system 300 may include a transmitter (not shown) coupled to the processor 304 and the antenna 318 for transmitting signals back to the telemetry unit 306 or another unit capable of receiving the signals. For example, the electrical stimulation system 300 may transmit signals indicating whether the electrical stimulation system 300 is operating properly or not or indicating when the battery needs to be charged or the level of charge remaining in the battery. The processor 304 may also be capable of transmitting information about the pulse characteristics so that a user or clinician can determine or verify the characteristics.

Figure 4A:
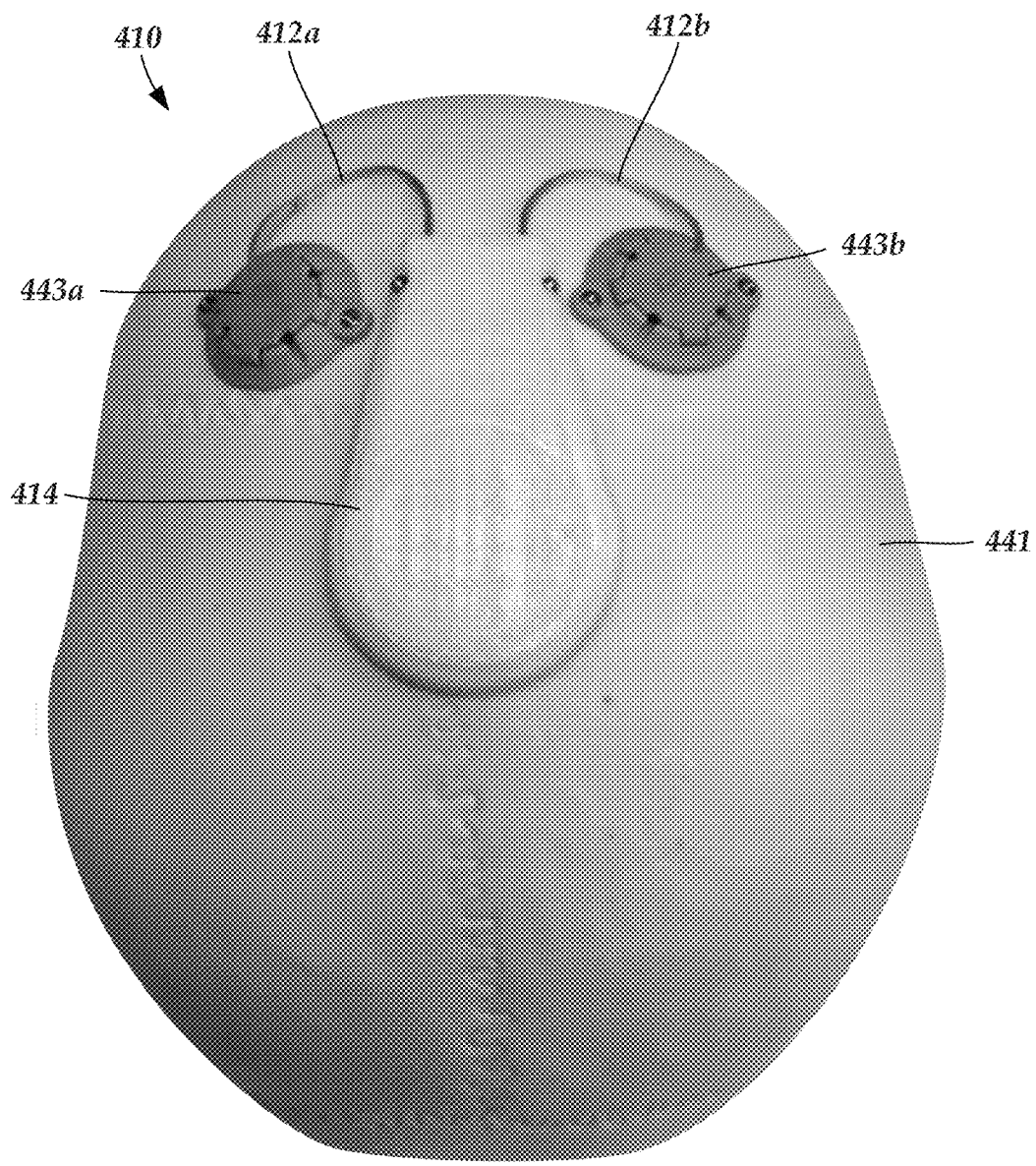
FIG. 4A is a schematic top view of one embodiment of a low-profile control module disposed along an outer surface of a skull and two leads extending from the control module and into the skull via burr holes covered with burr-hole covers, according to the invention.
Figure 4B:
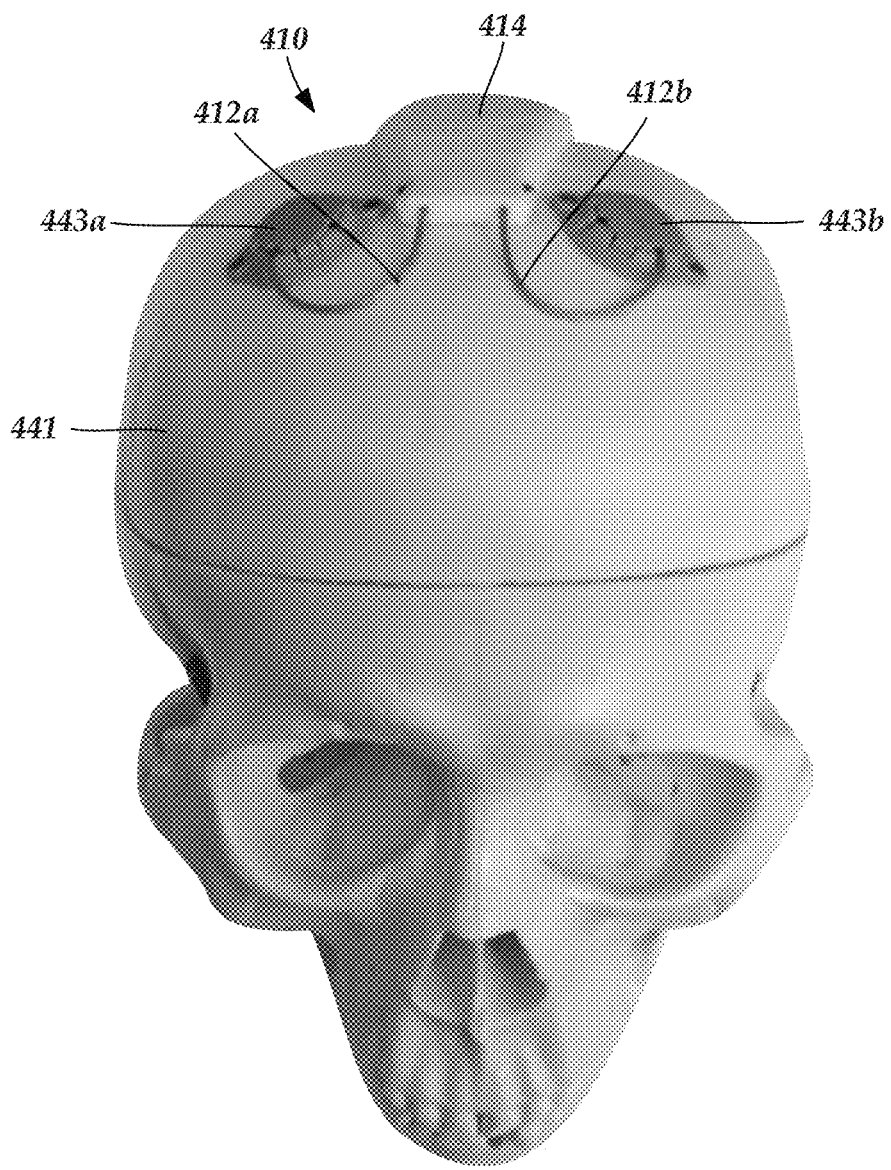
FIG. 4B is a schematic front view of one embodiment of the low-profile control module of FIG. 4A disposed along an outer surface of a skull and two leads extending from the control module and into the skull via burr holes covered with burr-hole covers, according to the invention.

Turning to FIGS. 4A-4B, conventional control modules (e.g., IPG 14) include power sources, electronics, and connector assemblies that collectively create a size and shape that may limit the locations where the control module can be implanted. At least some conventional control modules stack a battery above, below and/or adjacent to the main electronic subassembly, thereby forming a hermetic enclosure of a size or shape that limits potential implantation locations. In some instances, the size or shape of a control module may prevent the control module from physically fitting within a desired implantation location. In other instances, although a control module may physically fit within a desired implantation location, the size or shape of the control module may result in an undesirable cosmetic issue, such as the control module causing visible bulging of patient tissue.

In the case of deep brain stimulation, leads are typically extended through burr holes drilled into the patient's skull with the control module either implanted below the patient's clavicle area or disposed in a recessed region formed along an outer surface of the patient's skull. In the case of the former, the leads are undesirably tunneled along patient tissue from the burr holes in the skull to the patient's clavicle. Accordingly, such as technique may involve undesirably forming a lengthy tunnel along patient tissue. In the case of the latter, a medical practitioner needs to carve out a section of skull large enough to position the control module within the carved-out region. Such a technique is time-consuming and tedious for the medical practitioner, and invasive for the patient.

As described herein, a low-profile control module can be implanted into a patient. The low-profile control module ("control module") may increase the number of locations within a patient where a control module is implantable. Furthermore, the control module may also improve patient cosmetics, by reducing undesirable bulging of patient tissue caused by the control module.

For illustrative purposes, the control module is described herein relative to use for deep brain stimulation. It will be understood, however, that the control module can be used for applications other than deep brain stimulation, including peripheral nerve stimulation (e.g., occipital nerve stimulation, pudental nerve stimulation, or the like), spinal cord stimulation, dorsal root ganglion stimulation, sacral nerve stimulation, or stimulation of other nerves, muscles, and tissues.

In at least some embodiments, the control module is suitable for disposing over the patient's skull and beneath the patient's scalp. In at least some embodiments, the control module is attachable to an outer surface of the patient's skull without being inset into a recess carved into the skull. In at least some embodiments, when mounted to an outer surface of a patient's skull, the control module extends radially outwardly from the outer surface of the skull by no more than 20 mm, 18 mm, 16 mm, 14 mm, 12 mm, 10 mm, 9, mm, 8 mm, 7 mm, 6 mm, 5 mm, 4 mm, or 3 mm.

The below-described control module reduces a height dimension of the control module, as compared to conventional control modules, by removing the power supply from the electronics housing and, instead, positioning the power supply in a power assembly disposed laterally from the electronics housing, while still maintaining the power supply within the same sealed cavity as an electronic subassembly within the electronics housing. In some embodiments, the power assembly and one or more connector assemblies are each lateral to the electronics housing. Accordingly, when, for example, the control module is disposed along an anatomical structure, such as a patient's skull, each of the electronics housing, the power supply, and the connector assembly are positioned lateral to one another and do not overlap.

FIG. 4A shows, in top view, one embodiment of an electrical stimulation system 410 that includes a control module 414 disposed along an outer surface of a skull 441. FIG. 4B shows the electrical stimulation system 410 and skull 441 in front view. Two leads 412a, 412b extend from the control module 414 and into the skull 441 via burr holes, over which burr hole covers 443a, 443b, respectively, are disposed.

Figure 8A:
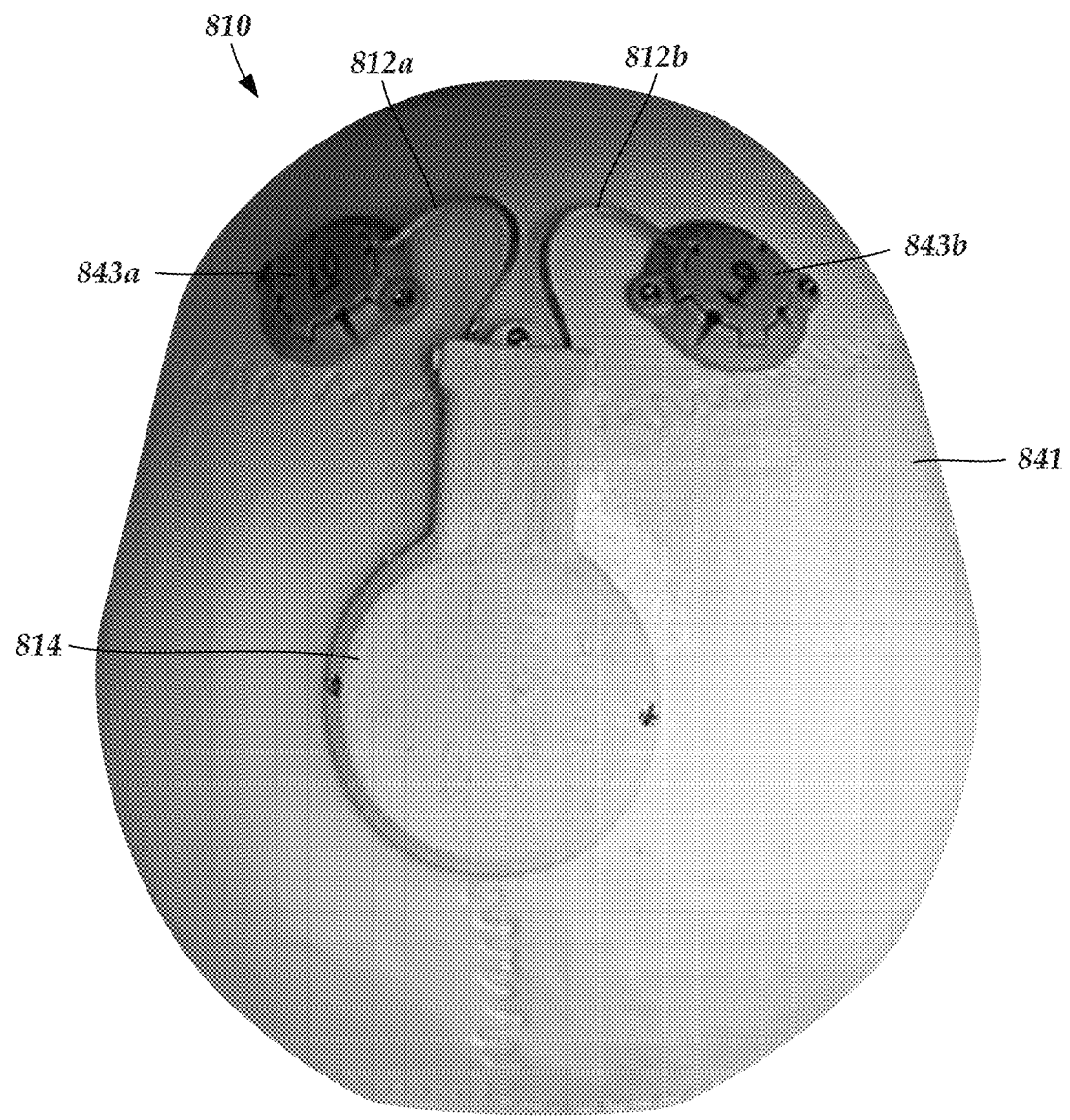
FIG. 8A is a schematic top view of another embodiment of a low-profile control module disposed along an outer surface of a skull and two leads extending from the control module and into the skull via burr holes covered with burr-hole covers, according to the invention.
Figure 8B:
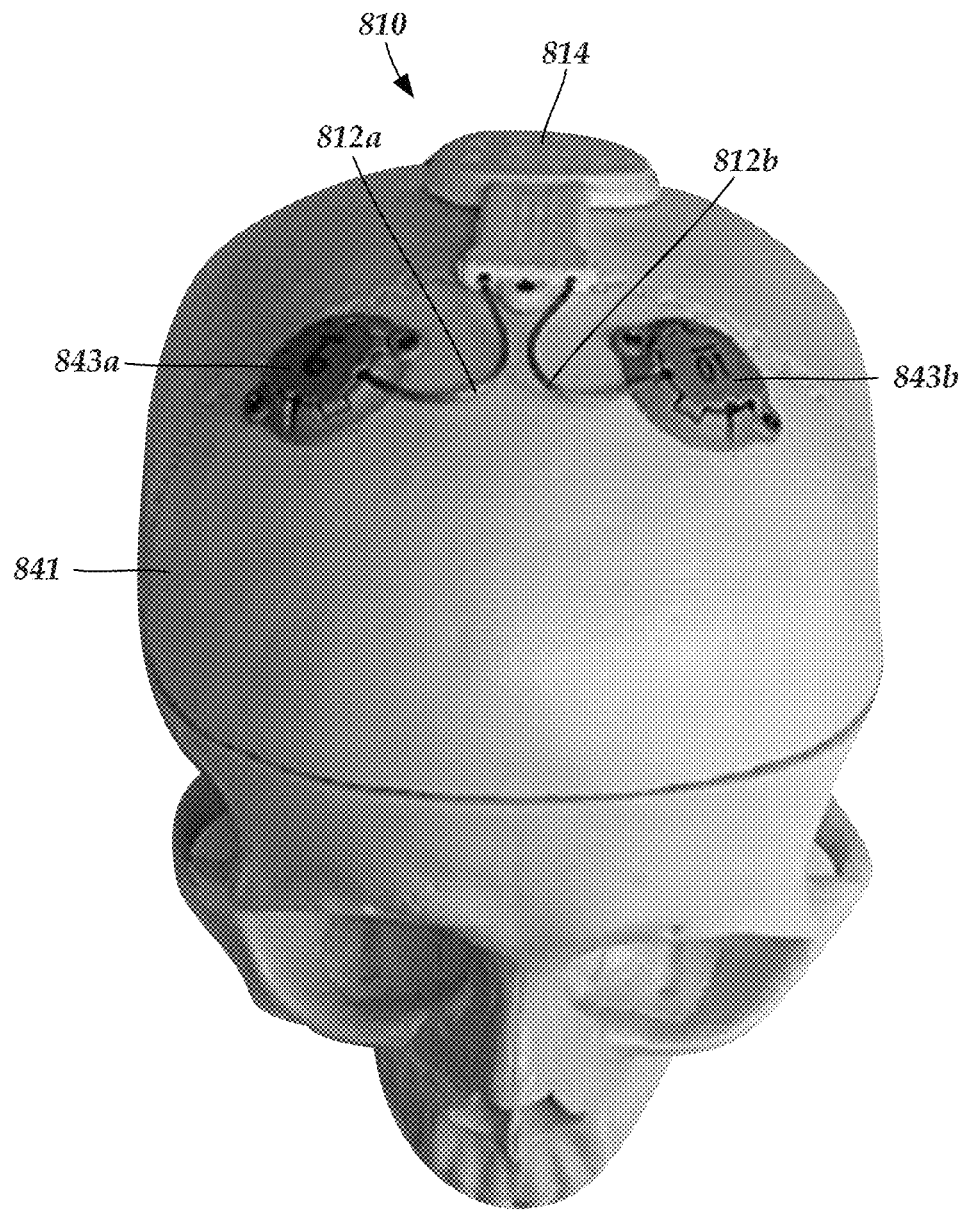
FIG. 8B is a schematic front view of one embodiment of the low-profile control module of FIG. 8A disposed along an outer surface of a skull and two leads extending from the control module and into the skull via burr holes covered with burr-hole covers, according to the invention.

FIG. 8A shows, in top view, another embodiment of an electrical stimulation system 810 that includes a control module 814 disposed along an outer surface of a skull 841. FIG. 8B shows the electrical stimulation system 810 and skull 841 in front view. Two leads 812a, 812b extend from the control module 814 and into the skull 841 via burr holes, over which burr hole covers 843a, 843b, respectively, are disposed.

As shown in FIGS. 4A-4B and 8A-8B, the control module extends radially outwards from the skull by approximately the same amount as the burr hole covers. Accordingly, when a patient's scalp is subsequently repositioned over the skull, the bulging caused by the control module may be less than would be possible with a conventional control module without undesirably disposing the conventional control module in a recess carved out of the skull.

Figure 5A:
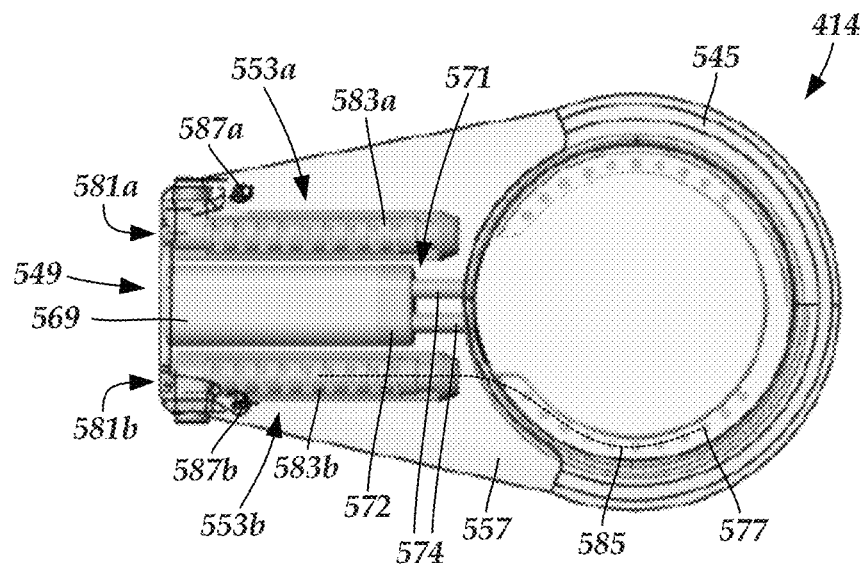
FIG. 5A is a schematic top view of one embodiment of a low-profile control module, the control module including a connector assembly and a sealed cavity formed collectively from an electronics housing and a power assembly, according to the invention.
Figure 5B:
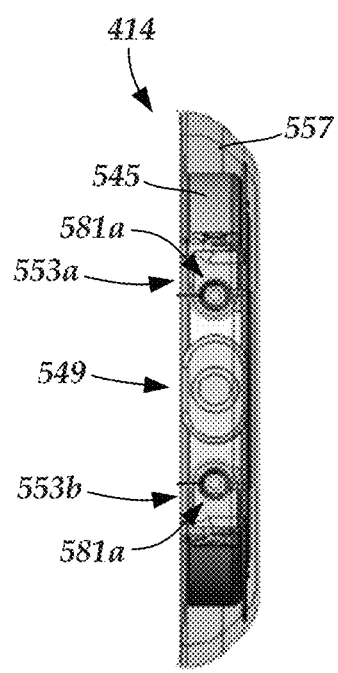
FIG. 5B is a schematic end view of one embodiment of the low-profile control module of FIG. 5A, according to the invention.
Figure 5C:
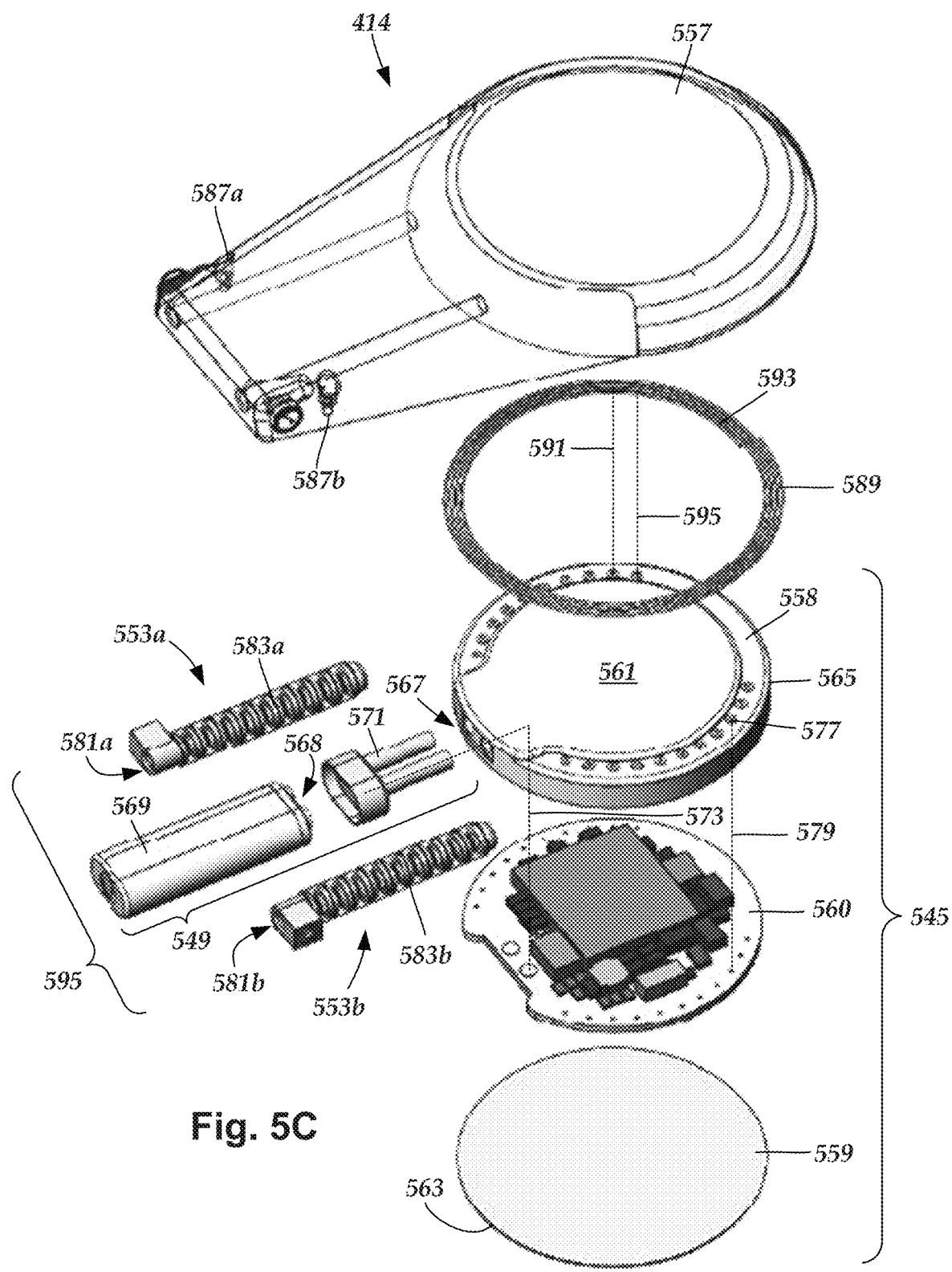
FIG. 5C is a schematic perspective, exploded view of one embodiment of the low-profile control module of FIG. 5A, according to the invention.

FIG. 5A shows, in schematic top view, one embodiment of the control module 414. FIG. 5B shows the control module 414 in end view. FIG. 5C shows the control module 414 in exploded, perspective view. The control module 414 includes an electronics housing 545, a power assembly 549, one or more connector assemblies 553a, 553b, and a covering 557 disposed over at least a portion of each of the electronics housing 545, the power assembly 549, and the connector assemblies 553a, 553b.

As will be described in more detail below, the electronics housing 545 and the power assembly 549 collectively form a sealed cavity. In at least some embodiments, the sealed cavity is hermetically sealed. As shown in FIG. 5C, in at least some embodiments the electronics housing 545 includes a top piece 558 and a bottom piece 559 that can be attached (e.g., laser welded) to the top piece 557 to form a sealed environment within the electronics housing 545. An electronic subassembly 560 is disposed in the electronics housing 545. In at least some embodiments the electronic subassembly 560 includes a printed circuit board assembly. The electronics housing can be formed from any biocompatible material suitable for providing a sealed environment. In at least some embodiments, the electronics housing is formed from a material suitable for being laser welded. In at least some embodiments, the electronics housing is formed from titanium.

In at least some embodiments, the electronics housing 545 is disc-shaped, with a first major surface 561, an opposing second major surface 563, and a side surface 565 extending between the opposing major surfaces 561, 563. In at least some embodiments, the first and second major surfaces are parallel to one another. In some embodiments, the side surface 565 has a length, or height, (the shortest distance between the first and second major surfaces) that is no more than 20 mm, 18 mm, 16 mm, 14 mm, 12 mm, 10 mm, 9, mm, 8 mm, 7 mm, 6 mm, 5 mm, 4 mm, or 3 mm.

Multiple feedthrough pins, such as feedthrough pin 577, are disposed along an outer surface of the electronics housing 545. The feedthrough pins can be disposed at any suitable location along the outer surface of the electronics housing. In the illustrated embodiments, the feedthrough pins are disposed along the periphery of the first major surface 561. The feedthrough pins enable components external to the sealed cavity to electrically couple with the electronic subassembly within the sealed cavity. The feedthrough pins are electrically coupled to the electronic subassembly 560, as shown schematically in FIG. 5C, by a dotted line 579. The feedthrough pins are electrically insulated from the electronics housing.

One or more power apertures 567 are defined along the electronics housing 549.

In FIGS. 5A-5C, two power apertures are shown extending through the side surface 565. The power assembly 549 attaches to the power apertures 567 and extends outwardly therefrom to form a sealed environment therebetween. In the illustrated embodiments, the power assembly extends laterally outwardly from the electronics housing. As mentioned above, the electronics housing 545 and the power assembly 549 collectively form a sealed cavity.

The power assembly 549 includes one or more power supplies 569, such as one or more batteries, disposed within the sealed cavity, yet the outside of the electronics housing 545. In at least some embodiments, the power supply 569 is coupled directly to the electronics housing (e.g., via the power apertures). In other embodiments, the power assembly 549 includes at least one conduit assembly 571 extending between the power supply 569 and the electronics housing 545. In at least some embodiments, the power assembly includes multiple structures extending from (and forming a sealed environment with) the housing, where at least two of the multiple structures includes a different power source.

As shown in FIG. 5A, the conduit assembly 571 includes a coupler 572 coupled, or coupleable, to one or more tubular conduits 574. The coupler 574 is coupled to, and forms a sealed connection with, the power supply 569. The one or more tubular conduits 574 of the conduit assembly(s) 571 are coupled to, and form a sealed connection with, the electronics housing 545 (e.g., via the power apertures). In at least some embodiments, one or more of the sealed connections along the electronics housing or the power assembly, or therebetween, is formed via laser welding.

The coupler 574 is disposed over power-supply contacts 568 of the power supply 569. Note that the power supply may include a power-supply feedthrough assembly coupled to the power-supply contacts and extending through a shell of the power supply. The coupler 574 forms a sealed connection with the portion of the power supply 569 that includes the power-supply contacts. In some embodiments, the coupler 574 is disposed over a portion of the power supply 569. In other embodiments, the coupler 574 is disposed over the entire power supply 569, thereby sealing the entire power supply within the coupler 574. The one or more tubular conduits 574 are of sufficient size to receive one or more power conductors 573 for electrically coupling the power supply 569 to the electronic subassembly 560.

In FIG. 5C, one of the power conductors 573 is shown schematically as a dotted line extending from along the conduit assembly 571 to a connection along the electronic subassembly 560. In the illustrated embodiment, the conduit assembly 571 includes separate anode and cathode conduits for facilitating electrical separation of an anode power conductor from a cathode power conductor. In at least some embodiments, the top and bottom pieces of the electronics housing are sealed (e.g., laser welded) after the one or more power conductors are electrically coupled to the electronic subassembly.

One or more connector assemblies extend laterally from the electronics housing. In some embodiments, the control module includes a single connector assembly. In other embodiments, the control module includes multiple connector assemblies. In the illustrated embodiment, the control module includes two connector assemblies 553a, 553b. The connector assemblies 553a, 553b are each configured and arranged to receive a single lead.

The connector assemblies 553a, 553b define connector lumens 581a, 581b, respectively. Each connector assembly 553a, 553b is configured to receive a proximal portion of a lead. An array of connector contacts, such as connector contacts 583a, 583b, is arranged along each of the connector lumens 581a, 581b, respectively, and is configured to electrically couple with terminals of the leads when the proximal portions of the leads are received by the connector assemblies. The connector contacts can be electrically isolated from one another by electrically-nonconductive spacers. The connector assemblies may, optionally, include end stops to promote alignment of the lead terminals with the connector contacts.

The connector contacts 583a, 583b are electrically coupled to the electronic subassembly 560. In at least some embodiments the electronic subassembly 560 is disposed in a sealed cavity, while the connector assemblies are external to the sealed cavity. Accordingly, in at least some embodiments connector conductors can be extended between the connector contacts and the feedthrough pins disposed along the electronics housing which, in turn, extend into the electronics housing and electrically couple with the electronic subassembly. As an example, in the embodiment illustrated in FIG. 5A, connector conductors, such as connector conductor 585, electrically couple the connector contacts, such as connector contact 583b of the connector assembly 553b, to the feedthrough pins 577 which, in turn, are coupled to the electronic subassembly 560 (as shown in FIG. 5C).

The connector assemblies can extend outwardly from the electronics housing 545 in any suitable direction. In the illustrated embodiments, the connector lumens 581a, 581b of the connector assembly extend approximately radially (e.g., +/−10°) outwards from the electronics housing. In which case, when proximal portions of leads are disposed in the connector assemblies, the proximal portions of the lead extend radially inwards towards the electronic subassembly, or the electronics housing, or both.

It may be advantageous to form the control module with the connector assembly abutting, or in close proximity to, the power assembly to collectively form a lateral unit 595 of the control module. In the illustrated embodiments, the lateral unit 595 is shown with the connector assemblies 553a, 553b flanking the power assembly 549, with the power assembly and connector lumens extending parallel to one another. Such an arrangement may provide increased structure to both the power assembly and connector assemblies, as well as facilitate electrical connections between the connector contacts and the feedthrough pins when the feedthrough pins are disposed on opposing sides of the electronics housing. Additionally, as described below with reference to FIGS. 7A-7B, in some embodiments, the power assembly is configured to bend. In which case, it may be advantageous for the connector assemblies to bend with the power assembly to facilitate implantation of the control module along a contoured surface.

The covering 557 is disposed over at least a portion of each of the electronics housing and the lateral unit to provide protection to the control module. In at least some embodiments, the covering 557 also seals at least a portion of each of the electronics housing, power assembly, and one or more connector assemblies. In at least some embodiments, the covering 557 is formed from an electrically-nonconductive material to insulate the electrical components from one another and/or the patient. The covering can be formed from any suitable biocompatible material. In at least some embodiments, the covering 557 is formed from silicone.

In at least some embodiments, the covering 557 defines one or more fastener apertures, such as fastener apertures 587a, 587b, for receiving fasteners (e.g., screws, pins, or the like) suitable for fastening the control module to patient tissue. In at least some embodiments, at least one of the fastener apertures is disposed along the lateral unit of the control module. In at least some embodiments, the fastener apertures are configured to receive fasteners suitable for fastening the control module to an anatomical structure, such as an outer surface of a patient's skull (see e.g., FIGS. 4A-4B and 8A-8B).

In at least some embodiments, the control module 414 includes a charging coil 589. As shown schematically in FIG. 5C by dotted line 591, the optional charging coil can be coupled to the electronic subassembly via one or more of the feedthrough pins 577. In at least some embodiments, the control module 414 includes one or more antennas 593 (e.g., Bluetooth, or the like). As shown schematically in FIG. 5C by dotted line 595, the optional antenna(s) can be coupled to the electronic subassembly via one or more of the feedthrough pins 577. In at least some embodiments, the charging coil and antenna(s) are disposed external to the electronics housing. In at least some embodiments, the charging coil and antenna(s) are disposed beneath, or embedded within, the electrically nonconductive covering 557.

Figure 6:
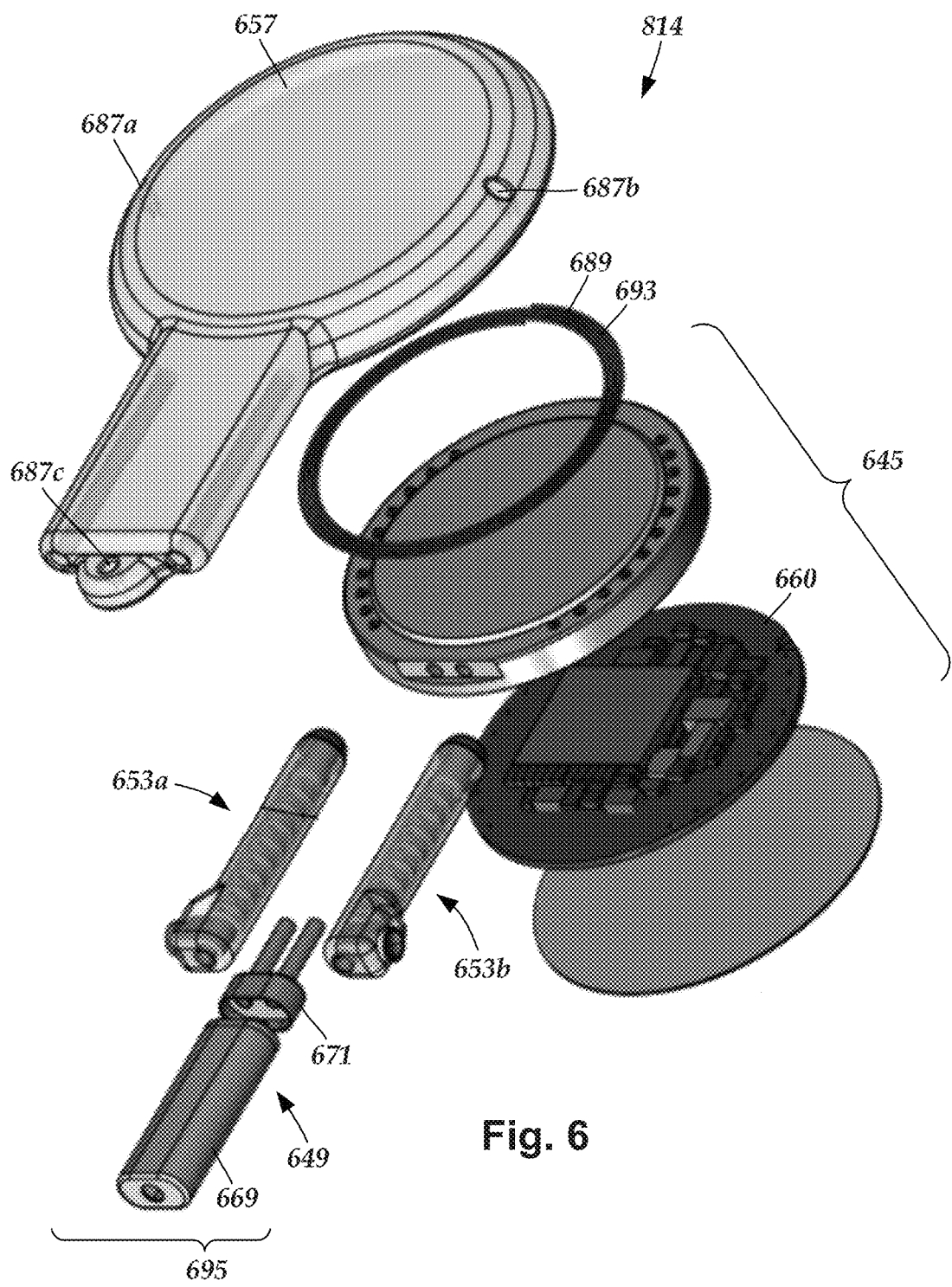
FIG. 6 is a schematic perspective, exploded view of an alternate embodiment of a low-profile control module including a connector assembly and a sealed cavity formed collectively from an electronics housing and a power assembly, according to the invention.

FIG. 6 shows, in schematic perspective, exploded view, the control module 814. The control module 814 includes an electronics housing 645, a power assembly 649, connector assemblies 653a, 653b, and a covering 657 disposed over at least a portion of each of the electronics housing 645, the power assembly 649, and the connector assemblies 653a, 653b. In the illustrated embodiment, the connector assemblies 653a, 653b are configured to receive two leads and include connector contacts electrically coupled to an electronic subassembly 660 disposed in the electronics housing 645.

The power assembly 649 is physically attached to the electronics housing 645 and extends laterally outwardly therefrom to collectively form a sealed cavity with the electronics housing. The power assembly 649 includes a power supply 669, such as one or more batteries, with power-supply contacts disposed within the sealed cavity, yet outside of the electronics housing 645. The power supply 669 is electrically coupled to the electronic subassembly 660. In the illustrated embodiment, the power assembly 649 includes a conduit assembly 671 extending between the power supply 669 and the electronics housing 645.

The connector assemblies 653a, 653b extend laterally outward from the electronics housing. In the illustrated embodiment, the power assembly 649 and the connector assemblies 653a, 653b collectively form a lateral unit 695 extending laterally from the electronics housing 645. In the illustrated embodiment, the power assembly extends approximately radially (e.g., +/−10°) outwards from the electronics housing and connector lumens of the connector assembly extend parallel to the power assembly. In at least some embodiments, the control module 814 includes a charging coil 689. In at least some embodiments, the control module 814 includes one or more antennas 693 (e.g., Bluetooth, or the like).

The control module 814 includes a differently-shaped covering 657 from the control module 414. As shown in FIG. 6, the portion of the 657 disposed over the power assembly 649 and the connector assemblies 653a, 653b (i.e., the lateral unit 695) has a smaller lateral profile than the corresponding portion of the covering 557 (see e.g., FIGS. 5A-5C). In at least some embodiments, the portion of the covering 657 disposed over the lateral unit 695 and extending radially from the electronics housing 645 has parallel opposing edges. In contrast, the portion of the covering 557 disposed over the lateral unit 595 (see e.g., FIGS. 5A-5C) and extending radially from the electronics housing 545 has tapered opposing edges extending outwardly from the electronics housing 645.

The covering 657 defines fastener apertures 687a-c. The fastener apertures can be disposed along any portion of the covering 657 suitable for anchoring the control module 814 to patient tissue. In the illustrated embodiment, the fastener apertures 687a, 687b are defined along the portion of the covering 657 disposed over the electronics housing 645, while the fastener aperture 687c is defined along the portion of the covering 657 disposed over the lateral unit 695.

Figure 7A:
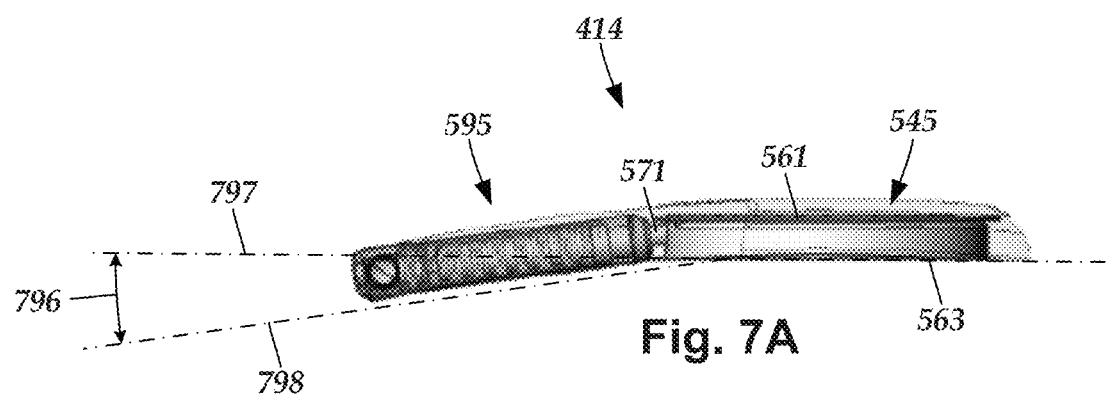
FIG. 7A is a schematic side view of one embodiment of the low-profile control module of FIG. 5A with the power assembly bent relative to the electronics housing, according to the invention.
Figure 7B:
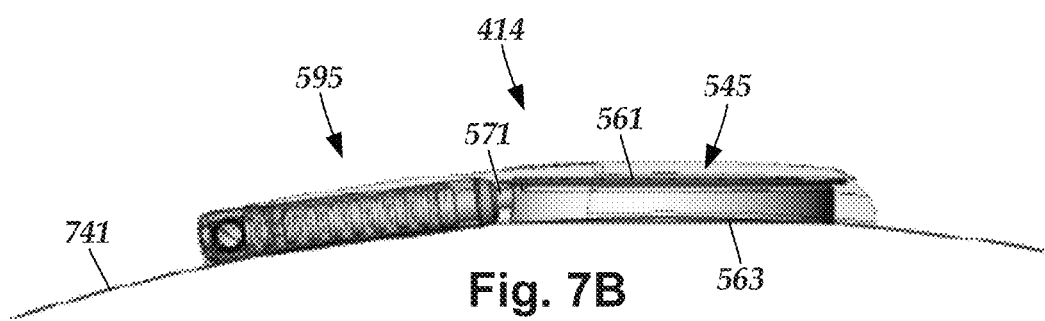
FIG. 7B is a schematic side view of one embodiment of the bent low-profile control module of FIG. 7A disposed along a patient's skull with the bending of the power assembly relative to the sealed electronics housing corresponding to a contour of the skull, according to the invention.

Turning to FIGS. 7A-7B, in some instances it may be advantageous for the power assembly to include at least one bend to enable the lateral unit of the control module to extend outwardly from the electronics housing out of plane with the major surfaces of electronics housing (i.e., at a non-180° angle relative to a major axis of the electronics housing). Providing such a bend may enable the control module to better conform to a curved surface when anchored to that surface than were the lateral unit to extend outwardly from the electronics housing in the same plane as the major surfaces of the electronics housing. In at least some embodiments, the power assembly includes a bend forming an angle that corresponds to a contour of an anatomical structure, such as a portion of an outer surface of a patient's skull to which the control module is attachable.

FIG. 7A shows one embodiment of the control module 414 in side view. As shown in FIG. 7A, the electronics housing extends along a plane 797 which, in at least some embodiments, is parallel to the first major surface 561 and the second major surface 563. The lateral unit extends from the electronics housing along a plane 798 that is not parallel to the plane 797 of the electronics housing. Instead, as shown in FIG. 7A, the plane 798 upon which the lateral unit 595 of the control module 414 extends forms an angle 796 with the plane 797.

In at least some embodiments, the bending of the lateral unit 595 relative to the electronics housing is enabled by a bend formed along the conduit assembly 571. The bend can form any suitable angle 796 including, for example, 1°, 2°, 3°, 4°, 5°, 6°, 7°, 8°, 9°, 10°, 15°, 20°, 25°, 30°, 35°, 40°, 45°, 50°, 60°, 70°, 80°, 90°, 100°, 110°, 120°, 130°, 140°, 150°, 160°, 170°, or more. In some embodiments, the bend is no smaller than 1° and no larger than 25°. In some embodiments, the bend is no smaller than 3° and no larger than 15°. In some embodiments, the bend is no smaller than 5° and no larger than 10°. In at least some embodiments, the angle 796 is acute. In at least some embodiments, the angle 796 corresponds to a contour of an anatomical structure (e.g., a portion of an outer surface of a patient's skull) to which the control module is attachable.

FIG. 7B shows, in schematic side view, one embodiment of the control module 414 attached to an outer surface of a skull 741. As shown in FIG. 7B, the control module is in a bent configuration with the lateral unit 595 out of plane with the major surfaces of the electronics housing. The angle of the bend corresponds to the contour of the skull 741 so that the control module extends along the skull and maintains a consistently low profile.

In some embodiments, the bend in the conduit assembly is formed during the manufacturing process. In some embodiments, the conduit assembly is formed from a material (e.g., a shape memory material, such as Nitinol) that is flexible enough to enable a medical practitioner to bend the conduit assembly, as needed, to provide a desired angle between the electronics housing and the lateral unit. In some embodiments, the conduit assembly is configured to maintain a given angle to which it is bent into until a subsequent external force is applied to the conduit assembly to change the angle of the bend. In other embodiments, the conduit assembly is configured to return to a given configuration when a force applied to the conduit assembly to form a bend of a particular angle is removed.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A control module for an electrical stimulation system, the control module comprising:
    an electronics housing having an outer surface;
    an electronic subassembly disposed within the electronics housing;
    a power assembly extending outwardly from the electronics housing and collectively with the electronics housing forming a sealed cavity, the power assembly comprising
        a power source, wherein the power source and the electronic subassembly are in the same sealed cavity,
        a conduit assembly extending from the power source to the electronics housing, and
        one or more power conductors extending along the conduit assembly and electrically coupling the power source to the electronic subassembly; and
    one or more connector assemblies, each of the one or more connector assemblies comprising:
        a connector lumen configured and arranged to receive a lead,
        a plurality of connector contacts arranged along the connector lumen and in electrical communication with the electronic subassembly, and
        a plurality of connector conductors electrically coupled to the connector contacts,
        wherein the one or more connector assemblies comprises a first connector assembly and a second connector assembly each extending laterally outwardly from the electronics housing, and wherein the first connector assembly and the second connector assembly flank the power assembly on opposite sides of the power assembly.

2. The control module of claim 1, wherein the conduit assembly comprises a coupler and one or more tubular conduits extending from the coupler, the coupler coupleable to the power source, the coupler and the one or more tubular conduits forming a portion of the sealed cavity, wherein the one or more power conductors extend through the one or more tubular conduits.

3. The control module of claim 2, wherein the one or more tubular conduits are two tubular conduits and the one or more power conductors are two power conductors, wherein a different one of the two power conductors extends along each of the two tubular conduits.

4. The control module of claim 2, wherein the one or more tubular conduits are flexible to permit bending relative to the electronics housing and power source upon application of a force and are configured to maintain a bent configuration.

5. The control module of claim 2, wherein the one or more tubular conduits are formed from a shape memory material.

6. The control module of claim 2, wherein the one or more tubular conduits comprise a bend forming an angle that is no smaller than 3° and no larger than 10°.

7. The control module of claim 6, wherein the angle of the bend corresponds to a contour of a portion of an outer surface of a skull to which the control module is attachable.

8. The control module of claim 6, wherein the electronics housing comprises opposing parallel major surfaces extending along a first plane, and wherein the bend causes the power assembly to extend along a second plane that is different from the first plane.

9. The control module of claim 1, further comprising a plurality of feedthrough pins extending through the electronics housing, wherein the conductors of the one or more connector assemblies are electrically coupled to the feedthrough pins and the feedthrough pins are electrically coupled to the electronic subassembly.

10. The control module of claim 9, further comprising a charging coil disposed on top of the electronics housing and coupled to at least one of the feedthrough pins.

11. The control module of claim 9, further comprising one or more antennas disposed on top of the electronics housing and coupled to at least one of the feedthrough pins.

12. The control module of claim 1, further comprising a covering disposed over at least a portion of each of the electronics housing, the power assembly, and the one or more connector assemblies.

13. The control module of claim 12, further comprising a fastener aperture defined in the covering, the fastener aperture configured and arranged to receive a fastener for fastening the control module to an outer surface of a skull.

14. The control module of claim 13 wherein, when the control module is configured for fastening to an outer surface of a skull, the control module extends radially outwards from the outer surface of the skull by an amount no greater than 7 mm.

15. An electrical stimulation system comprising:
the control module of claim 1; and
an electrical stimulation lead coupleable to the control module.

16. A control module for an electrical stimulation system, the control module comprising:
an electronics housing having an outer surface;
an electronic subassembly disposed within the electronics housing;
a power assembly extending laterally outwardly from the electronics housing and collectively with the electronics housing forming a sealed cavity, the power assembly comprising
a power source, wherein the power source and the electronic subassembly are in the same sealed cavity, and
one or more power conductors disposed entirely in the sealed cavity and electrically coupling the power source to the electronic subassembly; and
one or more connector assemblies extending laterally outwardly from the electronics housing, each of the one or more connector assemblies comprising:
a connector lumen configured and arranged to receive a lead,
a plurality of connector contacts arranged along the connector lumen and in electrical communication with the electronic subassembly, and
a plurality of connector conductors electrically coupled to the connector contacts, wherein the one or more connector assemblies comprises a first connector assembly and a second connector assembly each extending laterally outwardly from the electronics housing, and wherein the first connector assembly and the second connector assembly flank the power assembly on opposite sides of the power assembly.

17. A method for making the control module of claim 1, the method comprising:
disposing the electronic subassembly in the electronics housing;
attaching the power assembly having the power source to at least one aperture defined in the electronics housing to create a sealed connection between the power assembly and the electronics housing;
electrically coupling the power source to the electronic subassembly;
sealing the electronics housing to, collectively with the power assembly, form the sealed cavity; and
electrically coupling a connector assembly to the electronic subassembly, the connector assembly configured and arranged to receive a lead.

18. The method of claim 17, wherein attaching the power assembly having the power source to at least one aperture defined in the electronics housing comprises attaching the power source and the electronics housing to opposing ends of the conduit assembly.

19. The method of claim 18, further comprising bending the conduit assembly relative to the electronics housing and power source.

20. The method of claim 17, further comprising coupling a charging coil and one or more antennas to the electronic subassembly.

* * * * *